United States Patent
Umemura

(10) Patent No.: US 7,628,536 B2
(45) Date of Patent: Dec. 8, 2009

(54) MICROSCOPE APPARATUS

(75) Inventor: Izumi Umemura, Hiratsuka (JP)

(73) Assignee: Nikon Corporation, Tokyo (JP)

(*) Notice: Subject to any disclaimer, the term of this patent is extended or adjusted under 35 U.S.C. 154(b) by 0 days.

(21) Appl. No.: 12/314,478

(22) Filed: Dec. 11, 2008

(65) Prior Publication Data

US 2009/0103588 A1 Apr. 23, 2009

Related U.S. Application Data

(63) Continuation of application No. PCT/JP2007/061865, filed on Jun. 13, 2007.

(30) Foreign Application Priority Data

Jun. 13, 2006 (JP) .............................. 2006-163538

(51) Int. Cl.
G01N 21/09 (2006.01)
G12M 1/00 (2006.01)
G01N 23/04 (2006.01)

(52) U.S. Cl. .................... 374/141; 374/130; 435/288.7; 359/398; 250/309

(58) Field of Classification Search ............. 374/10–12, 374/30–39, 100, 141, 130, 120, 121, 131, 374/4–5; 250/309–311; 359/395, 398, 385; 435/303.1, 288.7; 382/133
See application file for complete search history.

(56) References Cited

U.S. PATENT DOCUMENTS

| | | | | |
|---|---|---|---|---|
| 3,654,091 A * | 4/1972 | Binnings et al. | ............. | 219/201 |
| 4,301,252 A * | 11/1981 | Baker et al. | ............. | 435/303.1 |
| 4,878,747 A * | 11/1989 | Sting et al. | ................. | 359/372 |
| 6,260,997 B1 * | 7/2001 | Claybourn et al. | ............ | 374/45 |
| 6,848,825 B1 * | 2/2005 | Simon et al. | ................ | 374/141 |
| 7,293,885 B2 * | 11/2007 | Kramer et al. | .............. | 359/601 |
| 7,382,531 B2 * | 6/2008 | Tsuchiya et al. | ............ | 359/395 |
| 7,476,857 B2 * | 1/2009 | Oosaki et al. | ............... | 250/310 |
| 7,557,988 B2 * | 7/2009 | Okugawa | ..................... | 359/395 |
| 2003/0016301 A1 * | 1/2003 | Aizaki et al. | ................ | 348/345 |
| 2005/0151587 A1 * | 7/2005 | Ozasa et al. | ................ | 330/253 |
| 2005/0282268 A1 * | 12/2005 | Kagayama | ............... | 435/288.7 |
| 2006/0014273 A1 * | 1/2006 | Yasuda et al. | ............ | 435/292.1 |
| 2006/0072190 A1 * | 4/2006 | Okugawa | ..................... | 359/368 |
| 2008/0221445 A1 * | 9/2008 | Rollins et al. | ............... | 600/428 |
| 2008/0247038 A1 * | 10/2008 | Sasaki et al. | ................ | 359/395 |
| 2008/0252967 A1 * | 10/2008 | Tomioka et al. | ............. | 359/398 |
| 2009/0121134 A1 * | 5/2009 | Oosaki et al. | ............... | 250/310 |
| 2009/0137030 A1 * | 5/2009 | Wada | ...................... | 435/288.7 |

(Continued)

FOREIGN PATENT DOCUMENTS

JP 2003270146 A * 9/2003

(Continued)

Primary Examiner—Gail Verbitsky
(74) Attorney, Agent, or Firm—Oliff & Berridge, PLC

(57) ABSTRACT

A microscope apparatus includes: a microscope unit; a chamber, arranged next to the microscope unit, that houses a specimen to be observed by the microscope unit; a humidifier, connected to the chamber, that humidifies the interior of the chamber; a chamber temperature sensor that measures a temperature within the chamber; a microscope temperature sensor that measures a temperature of the microscope unit; and a determination device that determines whether or not observation by microscope is possible based on outputs of the chamber temperature sensor and the microscope temperature sensor.

7 Claims, 7 Drawing Sheets

U.S. PATENT DOCUMENTS

2009/0161205 A1 * 6/2009 Harada et al. ............... 359/385

FOREIGN PATENT DOCUMENTS

| JP | A-2005-326495 | 11/2005 |
| JP | A-2006-039171 | 2/2006 |
| JP | A-2007-140155 | 6/2007 |
| WO | WO 2004109361 A1 * | 12/2004 |
| WO | WO 2007145233 A1 * | 12/2007 |

* cited by examiner

MICROSCOPE APPARATUS

This application is a continuation of International Application No. PCT/JP2007/061865 filed Jun. 13, 2007.

INCORPORATION BY REFERENCE

The disclosure of the following priority application is herein incorporated by reference:
Japanese Patent Application No. 2006-163538 filed Jun. 13, 2006; and
International Application No. PCT/JP2007/061865 filed Jun. 13, 2007.

BACKGROUND OF THE INVENTION

1. Field of the Invention
The present invention relates to a microscope apparatus.
2. Description of the Related Art
In the related art, tissue culture microscope apparatus equipped with a microscope apparatus and a culture apparatus for observing cultured cells are known (refer to patent document 1). A heating heater for internal temperature regulation, a humidifying heater for regulating internal humidity, a solenoid valve for supplying carbon dioxide gas connected to a carbon dioxide cylinder in order to regulate the concentration of carbon dioxide gas, and the like are provided at the culture apparatus of this culture microscope apparatus in order to regulate temperature and humidity etc. within a culture container placed in a chamber of the culture apparatus.

Such a culture microscope apparatus is disclosed in Japanese Laid-Open Patent Publication No. 2005-326495.

The apparatus described above is configured so as to control temperature within a chamber housing a specimen in order to observe the cells in a stable environment. Control is therefore exerted so that the temperature within the chamber falls within a prescribed temperature range without monitoring the temperature of the microscope apparatus. However, drifting (focus drift) of a focus position of a microscope occurs because the temperature of the microscope apparatus having a substantial heat capacity is not monitored. Images of cells being observed therefore become fuzzy, and in the worst case, fluctuation occurs in the X-Y direction and the observed portion shifts.

SUMMARY OF THE INVENTION

A microscope apparatus according to a first aspect of the present invention, includes: a microscope unit; a chamber, arranged next to the microscope unit, that houses a specimen to be observed by the microscope unit; a humidifier, connected to the chamber, that humidifies the interior of the chamber; a chamber temperature sensor that measures a temperature within the chamber; a microscope temperature sensor that measures a temperature of the microscope unit; and a determination device that determines whether or not observation by microscope is possible based on outputs of the chamber temperature sensor and the microscope temperature sensor.

According to a second aspect of the present invention, in the microscope apparatus according to the first aspect, it is preferable to further include a humidifier temperature sensor that measures a temperature of the humidifier, and it is preferable that the determination device determines whether or not observation by microscope is possible by further taking into consideration an output of the humidifier temperature sensor.

According to a third aspect of the present invention, in the microscope apparatus according to the second aspect, it is preferable to further include a notification device that notifies as to whether or not observation by microscope is possible, and it is preferable that the determination device determines that observation by microscope is possible when the chamber temperature, the humidifier temperature, and the microscope temperature become substantially stable, and causes the notification device to notify that observation by microscope is possible.

According to a fourth aspect of the present invention, in the microscope apparatus according to the second or third aspect, it is preferable to further include: an external air temperature sensor that measures an external air temperature, and it is preferable that the determination device determines whether or not observation by microscope is possible by further taking into consideration an output by the external air temperature sensor.

According to fifth aspect of the present invention, the microscope apparatus according to the fourth aspect may further include a chamber temperature setting circuit that sets the temperature of the chamber, with the external air temperature measured by the external air temperature sensor taken to be Tp, a chamber setting temperature set by the chamber temperature setting circuit taken to be Tc, and T1 and T2 taken to be constants, the determination device may cause the notification device to notify that the external air temperature is inappropriate when Tc−Tp is greater than T1, or when Tc−Tp is smaller than T2.

According to a sixth aspect of the present invention, the microscope apparatus according to the second aspect may further include: a humidifier temperature setting circuit that sets the temperature of the humidifier, with the chamber temperature measured by the chamber temperature sensor taken to be Tb, the humidifier temperature measured by the humidifier temperature sensor taken to be Th, the humidifier setting temperature set by the humidifier temperature setting circuit taken to be Tch, a maximum value for the microscope temperature measured by the microscope temperature sensor taken to be Tm and a minimum value for the microscope temperature measured by the microscope temperature sensor taken to be Tn, Tf taken to be a reference value, and Td1 and Td2 taken to be constants, the determination device may determine that observation by microscope is possible when:

(1) |Tb−Tc|<Td1, and this condition is maintained for a prescribed time or more;

(2) |Th−Tch|<Td2, and this condition is maintained for a prescribed time or more; and (3) (Tm−Tn)<Tf.

According to a seventh aspect of the present invention, in the microscope apparatus according to the third aspect, the determination device may estimate a period of time that elapses until when observation by microscope becomes possible based on the external air temperature measured by the external air temperature sensor, the chamber temperature measured by the chamber temperature sensor, the microscope temperature measured by the microscope temperature sensor, and the humidifier temperature measured by the humidifier temperature sensor, and may cause the notification device to notify of the estimated period of time.

According to the present invention, it is possible to prevent focus drift from occurring due to change in temperature of a microscope apparatus during observations.

DESCRIPTION OF PREFERRED EMBODIMENTS

Figure 1:
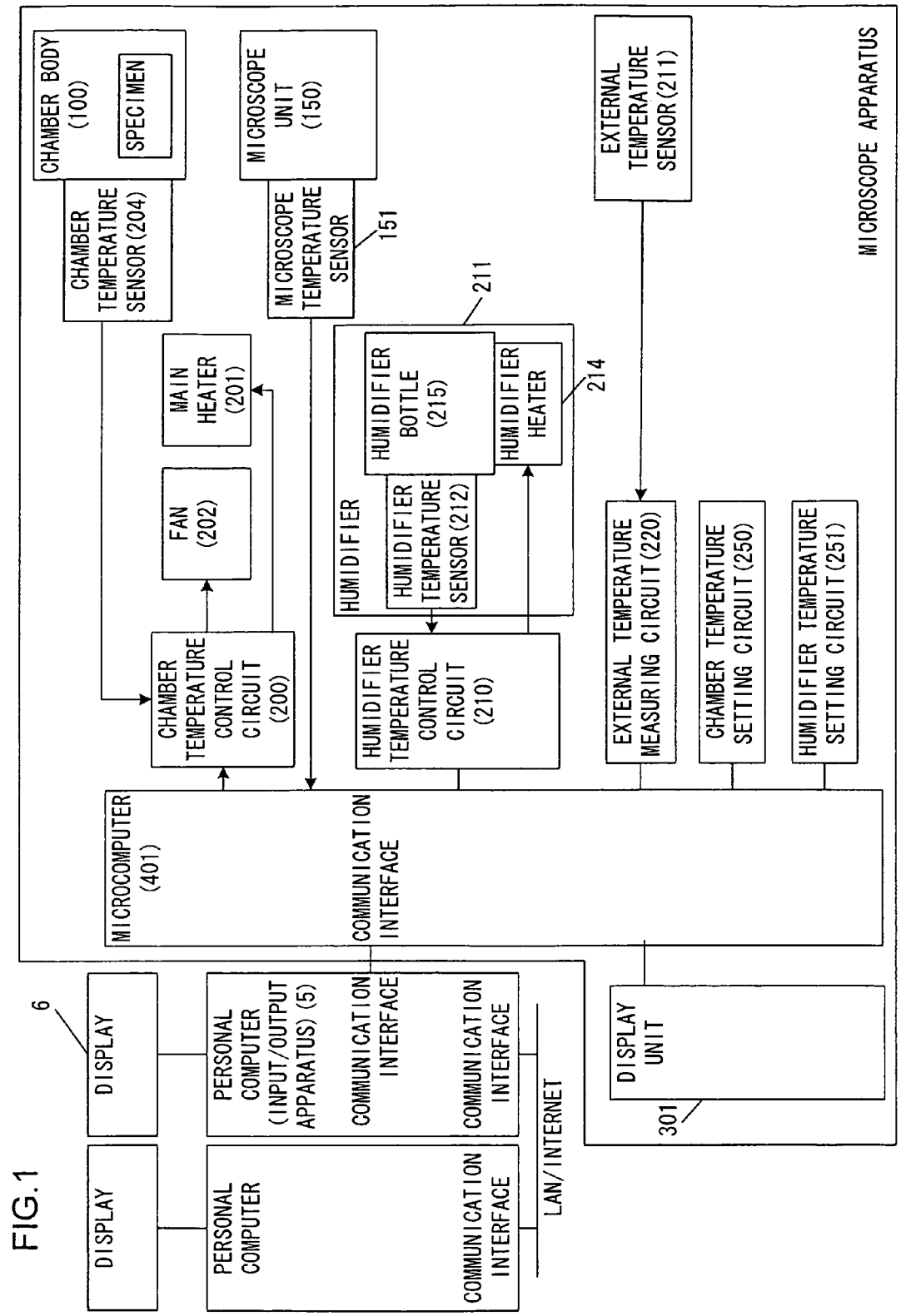
FIG. 1 is a block diagram showing a configuration for a microscope apparatus and its surroundings of a first embodiment of the present invention.
Figure 2:
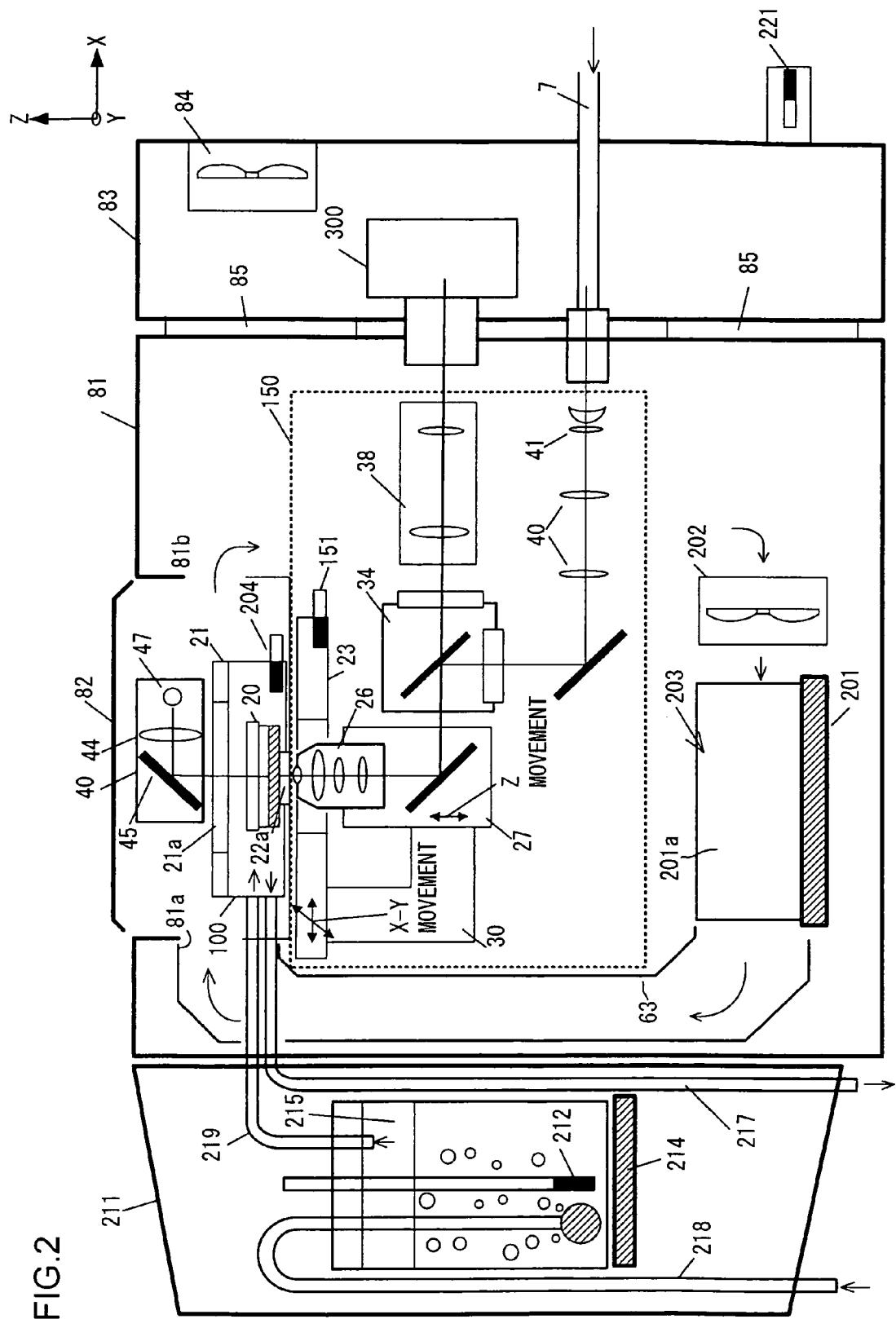
FIG. 2 is a conceptual view showing a configuration for the microscope apparatus shown in FIG. 1.

The following is an explanation based on the drawings of a preferred embodiment of a microscope apparatus of the present invention. FIG. 1 is a block diagram showing a configuration for a microscope apparatus and its surroundings of a first embodiment of the present invention, and FIG. 2 is a conceptual view showing a configuration for the microscope apparatus shown in FIG. 1.

This microscope apparatus is equipped with a microscope unit 150, a chamber body 100 disposed next to the microscope unit 150 for housing a specimen to be observed by the microscope unit 150, and a humidifier 211 for humidifying the interior of the chamber body 100. The chamber body 100 and the microscope unit 150 are housed in a first casing 81. The humidifier 211 and a second casing 83 for housing a coldproof camera 300 for taking microscope images of the specimen are connected to the first casing 81. As shown in FIG. 2, the microscope apparatus is constituted with the humidifier 211, the first casing 81, and the second casing 83.

The humidifier 211 is equipped with a humidifier bottle 215 with a cover, a heater 214, and a humidifier temperature sensor 212. The humidifier bottle 215 is filled with distilled water. The humidifier temperature sensor 212 detects the temperature of the distilled water. The heater 214 is provided below the humidifier bottle 215 and heats the distilled water up to a temperature set by a humidifier temperature setting circuit 251. An output signal of the humidifier temperature sensor 212 is inputted to a humidifier temperature control circuit 210. The humidifier temperature control circuit 210 controls the output of the heater 214 based on an output signal of the humidifier temperature sensor 212. An output signal of the humidifier temperature sensor 212 is outputted from the humidifier temperature control circuit 210 to a microcomputer 401. This output signal is used in order to ensure that the temperature within the humidifier 211 is within a prescribed range with respect to the set value and to determine whether the microscope apparatus is in a state where use is possible. A fixed amount of $CO_2$ mixture per unit time is then supplied from a $CO_2$ mixture source (not shown) to the distilled water of the humidifier bottle 215 via a silicon tube 218. When the distilled water is made to bubble as a result of the supply of the $CO_2$ mixture, the humidity of the $CO_2$ mixture within the humidifier bottle 215 becomes 95% or more. One end of a silicon tube 219 for supplying a humidified atmosphere to the chamber body 100 is open at the humidifier bottle 215.

The first casing 81 houses a transmission phase difference illumination optical system 40, the chamber body 100, the microscope unit 150, a heat exchanger 203, and a fan 202, etc.

The chamber body 100 is tightly closed by a chamber cover 21. A shielding glass 22a and a shielding glass 21a that enable optical observation by the microscope unit 150 are fitted at the bottom surface of the chamber body 100 and the chamber cover 21, respectively. The other end of the silicon tube 219 is open at the chamber body 100 and a fixed concentration of $CO_2$ mixture humidified by the humidifier bottle 215 is supplied to within the chamber body 100. A culture container (Petri dish 20) of transparent resin containing cultured cells is put into the chamber body 100. The Petri dish 20 is filled up with fluid (a culture medium, not shown) containing nutrient. It is therefore possible to suppress evaporation of the culture medium by maintaining the high-humidity $CO_2$ mixture within the chamber body 100, it is possible to keep the pH of the culture medium fixed, and the cells (specimen) can be made use of for a long time.

Further, one end of a silicon tube 217 is opened at the chamber body 100 in order to discharge $CO_2$ gas circulated within the chamber body 100 to outside. The other end of the silicon tube 217 is opened to the outside via the first casing 81 and the humidifier 211. The humidified atmosphere is isolated from the microscope unit 150. An optical system including an objective lens 26 of the microscope unit 150 and a drive unit (not shown) are therefore not exposed to the humidified atmosphere.

Further, a chamber temperature sensor 204 for measuring the temperature within the chamber body 100 the specimen is put into is provided at the chamber body 100. An output signal of the chamber temperature sensor 204 is inputted to a chamber temperature control circuit 200. The chamber temperature control circuit 200 controls the output of a main heater 201 so that the temperature of the chamber body 100 becomes the temperature set at a chamber temperature setting circuit 250. An output signal of the chamber temperature sensor 204 is outputted from the chamber temperature control circuit 200 to the microcomputer (determination device) 401. The output signal is used in order to ensure that the temperature within the chamber body 100 is within a prescribed range with respect to the set value and to determine whether the microscope apparatus is in a state where use is possible.

The transmission phase difference illumination optical system 40 includes an LED light source 47 that is a transmission illumination light source, a field lens 44, and a reflecting mirror 45. The microscope unit 150 includes a stage 23, the objective lens 26, a fluorescence filter cube 34, an image forming lens 38, a field lens 40, and a collector lens 41. Light emitted from the LED light source 47 is transmitted through the field lens 44, is reflected by the reflecting mirror 45, is transmitted through the shielding glass 21a of the chamber cover 21, and irradiates the specimen (not shown) within the Petri dish 20. Light transmitted by the specimen reaches a light receiving surface of the coldproof camera 300 within the second casing 83 via the shielding glass 22a, the objective lens 26, the fluorescence filter cube 34, and the image forming lens 38 so that an image of the specimen is formed.

The stage 23 is supported at a stage supporting member 30. The stage 23 is moved in an X-Y direction (a direction orthogonal to an optical axis of the objective lens 26) by a motor and rack-pinion mechanism (not shown) so as to change the position (i.e. an observation position for the specimen in an X-Y plane) of the specimen on the optical axis. A microscope temperature sensor 151 that detects the temperature of the microscope unit 150 is provided at the stage 23. An output signal of the microscope temperature sensor 151 is outputted to the microcomputer 401. The output signal can be used in order to judge whether the temperature fluctuation of the microscope unit 150 is within a fixed range, whether an extent of movement of a focal point of the microscope is small, and whether the microscope apparatus is in a state where use is possible.

The objective lens 26 is arranged on an optical axis of light emitted from the LED light source 47. Specifically, the objective lens 26 is arranged on an optical axis of light that is emitted from the LED light source 47 and is then bent by the reflecting mirror 45 before passing through the specimen within the chamber cover 21. The objective lens 26 is supported at an objective lens support member 27 so as to be moveable in a Z-axis direction. The objective lens support member 27 is driven by a motor (not shown) and the focus of the objective lens 26 is adjusted with respect to the specimen by moving the objective lens 26 in an optical axis direction (Z-axis) with respect to the specimen.

The fluorescence filter cube 34 splits light flux that is transmitted by the objective lens 26. A plurality of fluorescence filter cubes 34 are arranged in a direction orthogonal to the surface of the paper of FIG. 2 and it is possible to select different types of florescent cube filter according to the observation. Further, the image forming lens 38 is constituted with a plurality of different types of lenses. It is then possible to switch over the observation magnification by changing the image forming lens 38.

Illuminating light irradiated from a mercury lamp (not shown) by a fiber 7 is transmitted by the collector lens 41, the field lens 40, the fluorescence filter cube 34, the objective lens 26, and the shielding glass 22a so as to irradiate the specimen within the Petri dish 20. Fluorescence excited at the specimen reaches a light receiving surface of the coldproof camera 300 via the shielding glass 22a, the objective lens 26, the fluorescence filter cube 34, and the image forming lens 38, so that an image of the specimen is formed.

The heat exchanger 203 is arranged below the microscope unit 150. The heat exchanger 203 is constituted with the main heater 201 and an aluminum fin 201a.

The fan 202 is arranged to the rear of the heat exchanger 203 below the microscope unit 150. The fan 202 supplies air heated by the heat exchanger 203 to above the microscope unit 150 via a duct 63. A casing that contains the chamber body 100 and the transmission phase difference illumination optical system 40 is arranged above the microscope unit 150 and is provided with an opening 81a for receiving the duct 63. After recovering heat at the chamber body 100, air supplied to the surroundings of the chamber body 100 from the duct 63 via the opening 81a is discharged from an opening 81b provided in the casing. The air is then returned to below the microscope unit 150 and is again heated by the heat exchanger 203. Namely, the air is circulated within the first casing 81. The output of the main heater 201 and the fan 202 are controlled by the chamber temperature control circuit 200. The fan 202 is driven at maximum output when temperature control starts and is operated at a lower output after the temperature of the chamber body 100 reaches a set temperature.

A casing cover 82 for inserting and removing the Petri dish 20 holding the specimen is provided at an upper part of the first casing 81. The casing cover 82 simultaneously seals the opening of the first casing 81 and blocks out external light (lighting of the room by fluorescent light etc.).

The second casing 83 is coupled with the first casing 81 via a heat insulating member 85. The second casing 83 houses the coldproof camera 300, the fiber 7, and a fan 84. An external air temperature sensor 221 is provided at the outside of the second casing 83.

The fan 84 is used to discharge air heated by heat generated by the coldproof camera 300 and a substrate (not shown) to outside in order to maintain the temperature within the second casing 83 at approximately the external air temperature.

The external air temperature sensor 221 is arranged outside of the second casing 83 and measures the external air temperature where the microscope apparatus is located. An output signal of the external air temperature sensor 221 is outputted to the microcomputer 401 via an external air temperature measuring circuit 220 and is used to determine whether the microscope apparatus is at a temperature where operation is possible.

The microcomputer 401 is arranged within, for example, the second casing 83. The chamber temperature control circuit 200, the humidifier temperature control circuit 210, the external air temperature measuring circuit 220, the chamber temperature setting circuit 250, and the humidifier temperature setting circuit 251 are then connected to the microcomputer 401. The microcomputer 401 carries out overall control of these circuits and the microscope apparatus such as driving of the microscope unit 150. A display unit (notification device) 301 that displays the result as to whether the microscope apparatus is at a temperature where operation is possible based on the measured temperature of the chamber body 100, the temperature of the humidifier 211, and the external air temperature is connected to the microcomputer 401. The microcomputer 401 displays that observation with the microscope is possible at the display unit 301 when the outputs of the chamber temperature sensor 204, the microscope temperature sensor 151, and the humidifier temperature sensor 212 are within a prescribed temperature range. It is also possible for the microcomputer 401 and the display unit 301 to be removed and to be arranged outside of the microscope apparatus.

As shown in FIG. 1, a personal computer 5 is connected to the microscope apparatus. The personal computer 5 is connected to the microcomputer 401 of the microscope apparatus via a communication interface (communication IF) and an image of the specimen etc. obtained by the microscope apparatus is displayed at a display 6 so as to enable the microscope apparatus to be controlled from a remote location. It is also possible for, for example, control to be exerted via the personal computer 5 so as to move the microscope apparatus in an XYZ direction of the stage 23. It is therefore possible for the personal computer 5 to function as an input/output device for the microscope apparatus.

Figure 3:
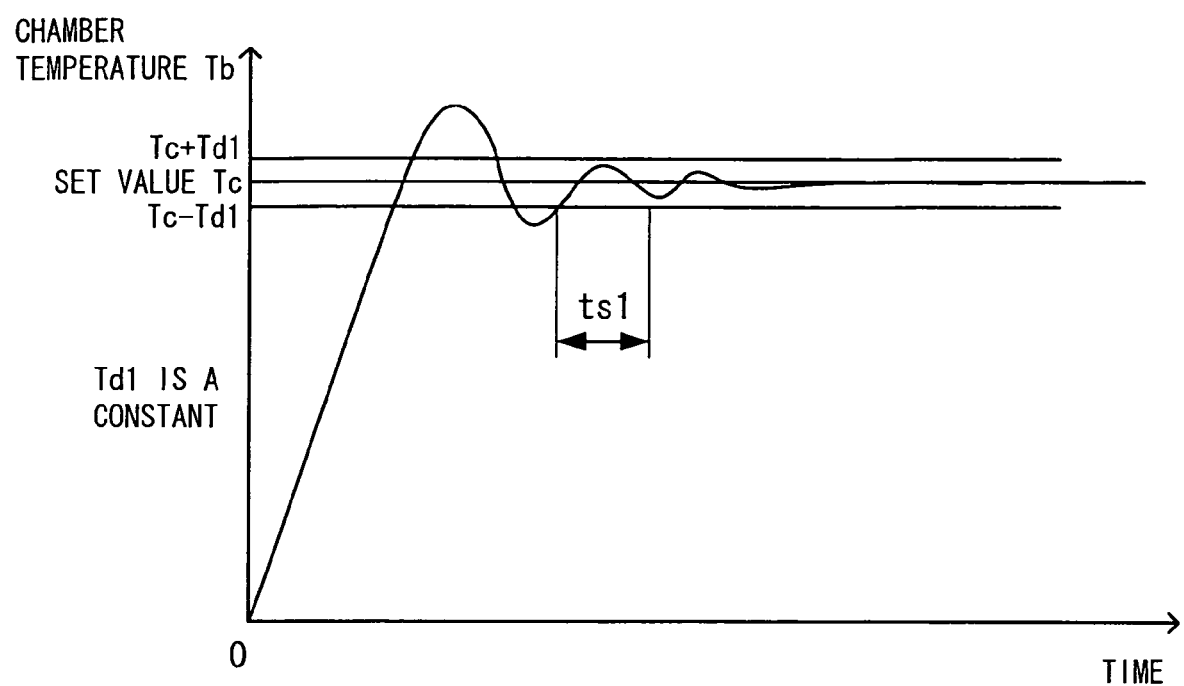
FIG. 3 is a diagram explaining determination of whether or not the temperature of a chamber body is stable.
Figure 4:
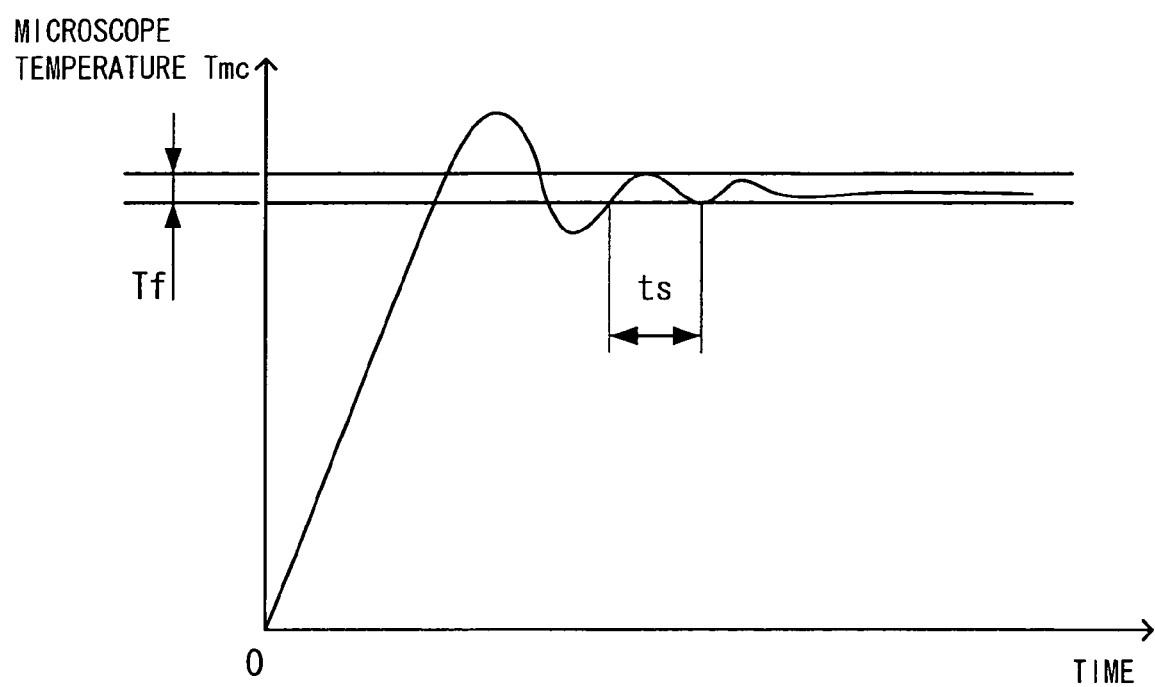
FIG. 4 is a diagram explaining determination of whether or not the temperature of a microscope unit is stable.
Figure 5:
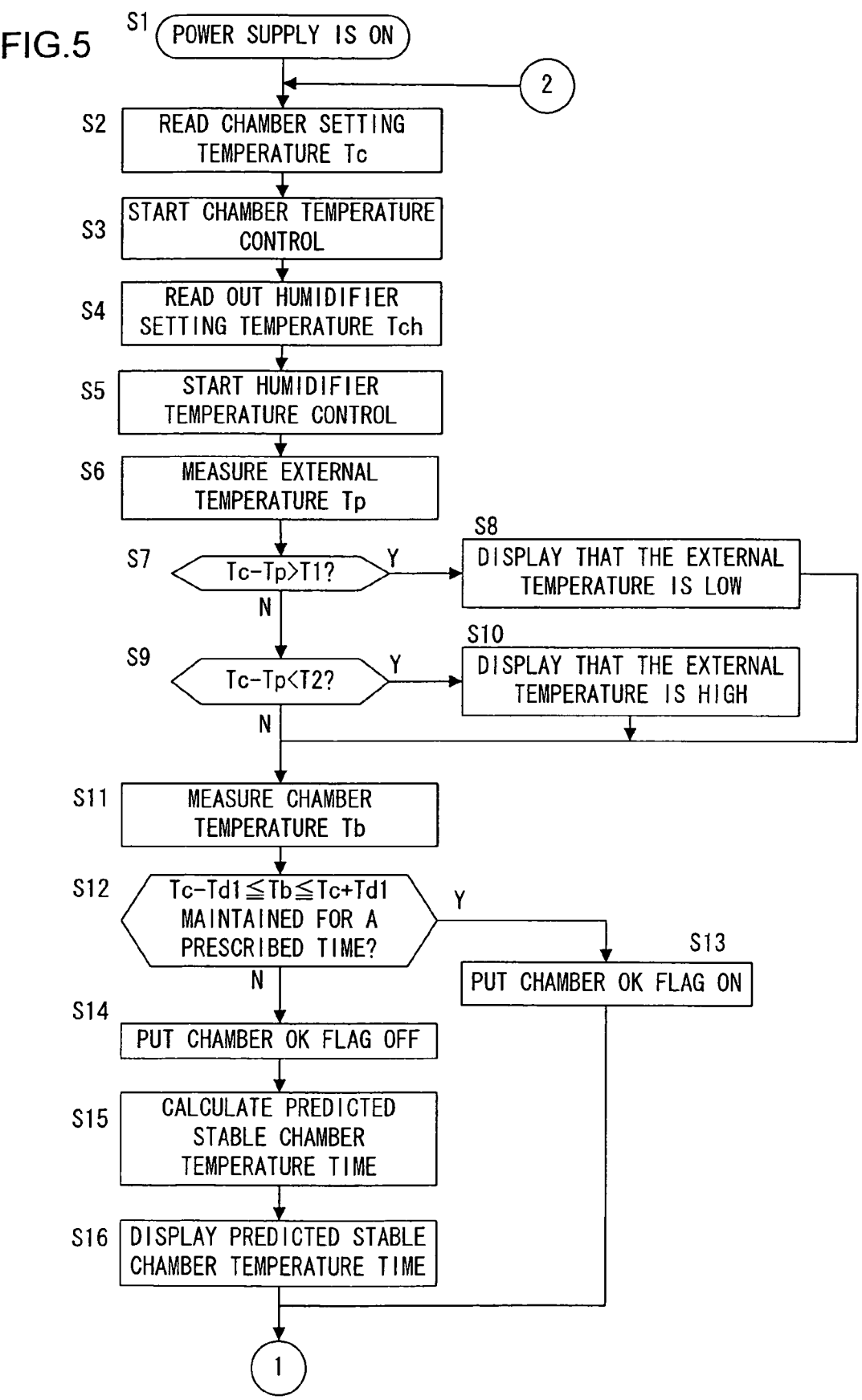
FIG. 5 is a flowchart explaining the flow of control for determining completion of preparation of the microscope apparatus for use based on external temperature, chamber temperature, humidifier temperature, and microscope temperature.
Figure 6:
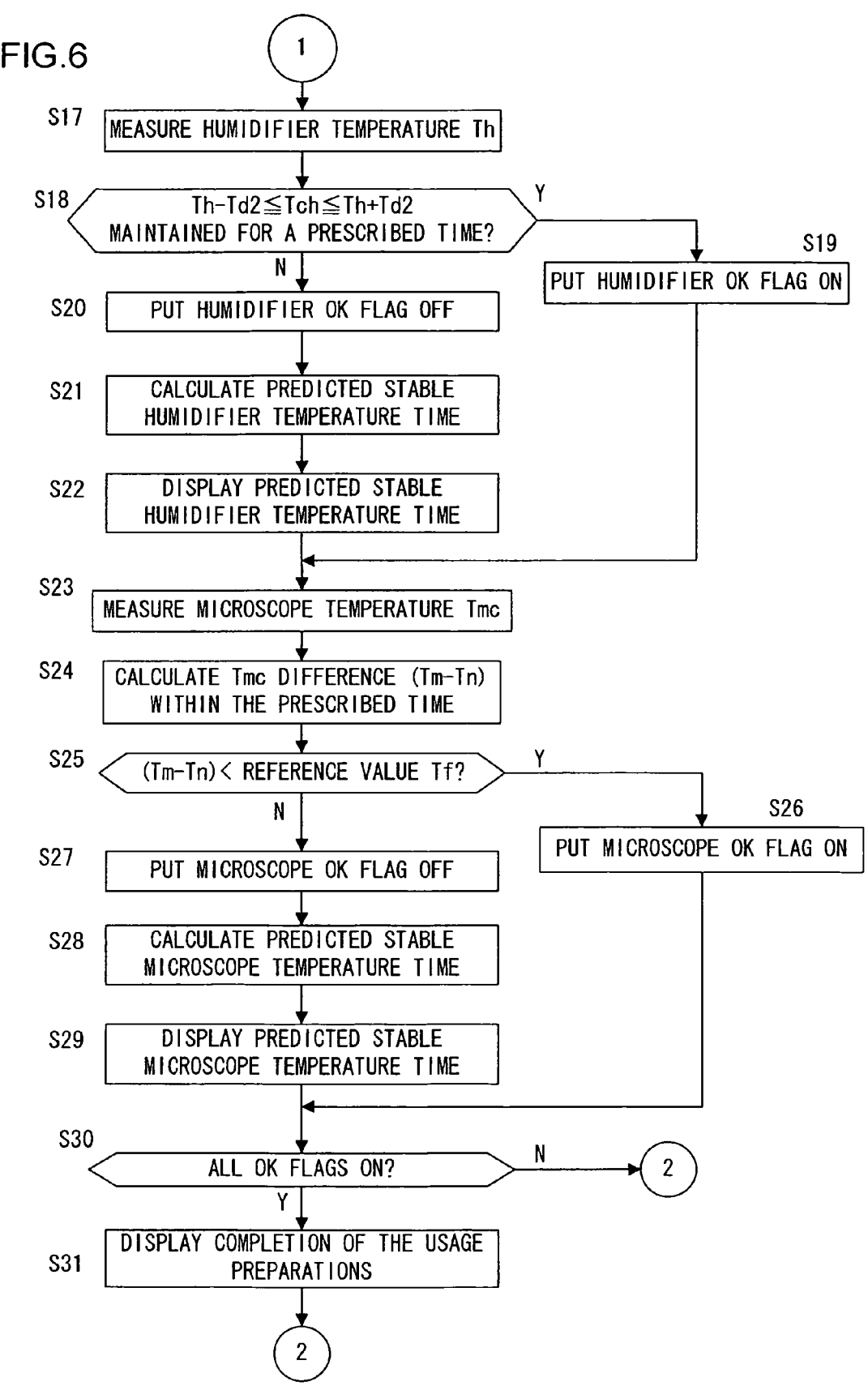
FIG. 6 is a flowchart continuing on from FIG. 5 explaining the flow of control for determining completion of preparation of the microscope apparatus for use based on external temperature, chamber temperature, humidifier temperature, and microscope temperature.

Next, a description is given of the operation of the microscope apparatus. FIG. 3 is a view illustrating a determination as to whether or not the temperature of the chamber body 100 is stable. FIG. 4 is a view illustrating a determination as to whether or not the temperature of the microscope unit 150 is stable. FIGS. 5 and 6 are flowcharts illustrating the flow of control for determining completion of preparation for use of the microscope apparatus based on the external temperature, the chamber temperature, the humidifier temperature, and the microscope temperature. This processing is basically controlled by the microcomputer 401. FIGS. 3 and 4 show time on the horizontal axis and temperature on the vertical axis.

First, a power supply of the microscope apparatus is turned on (S1).

Next, a chamber setting temperature Tc set in the chamber temperature setting circuit 250 is read out (S2). After this, chamber temperature control is started by the chamber temperature control circuit 200 (S3). Namely, the main heater 201 and the fan 202 are controlled so that control starts to regulate the temperature within the chamber body 100 to be the chamber setting temperature Tc.

Next, a humidifier setting temperature Tch set at the humidifier temperature setting circuit 251 is read out (S4). After this, humidifier temperature control by the humidifier temperature control circuit 210 is started (S5). Namely, the humidifier heater 214 is controlled so that control is started to regulate the temperature within the humidifier bottle 215 to be the humidifier setting temperature Tch.

Next, the external temperature Tp is measured by the external air temperature sensor 221, and a temperature signal indicating the measured external temperature Tp is converted to a digital signal by the external air temperature measuring circuit 220 and inputted to the microcomputer 401 (S6).

The microcomputer 401 determines whether or not Tc−Tp>T1 based on the acquired chamber setting temperature Tc and the external temperature Tp (S7). The temperature T1 is a constant decided from the output of the humidifier heater 214 and the heat retention performance of the microscope apparatus. For example, when the output of the humidifier heater 214 is large, or when the heat retention performance of the microscope apparatus is good, it is possible to use the microscope apparatus even if a difference between the temperature TC set for the chamber and the external temperature Tp is large. Typically, T1 is taken to be 25 degrees centigrade for a microscope apparatus where the chamber temperature can be set to 40 degrees centigrade when the room temperature, i.e., the external temperature Tp is 15 degrees centigrade. When Tc−Tp>T1 (Y), a control signal is outputted to the display unit 301, and it is indicated at the display unit 301 that the external temperature Tp is inappropriate, i.e. it is displayed that the external temperature Tp is too low with respect to the chamber setting temperature (S8).

When Tc−Tp is not greater than T1 (N), the microcomputer 40 then determines whether or not Tc−Tp<T2 (S9). T2 is a constant that is smaller than the constant T1. With the microscope apparatus of this embodiment, it is necessary for the chamber setting temperature Tc to be larger than the external temperature Tp. It is therefore possible for the microscope apparatus to be used when Tc>(Tp+Tu) taking into consideration a temperature rise Tu due to heat generated by the motor etc. within the microscope apparatus. Tu=T2. Typically, a rise in temperature due to heat by the motor etc. is in the order of five degrees centigrade so that, for example, T2=5 degrees centigrade. When Tc−Tp<T2 (Y), a control signal is outputted to the display unit 301 and it is displayed at the display unit 301 that the external air temperature Tp is inappropriate, i.e. it is displayed that the external temperature Tp is too high with respect to the chamber setting temperature Tc (S10).

After this, the temperature (chamber temperature Tb) of the chamber body 100 is measured by the chamber temperature sensor 204 and a signal for the measured chamber temperature Tb is inputted to the microcomputer 401 (S11).

The microcomputer 401 determines whether or not a state where the condition of Tc−Td1≦Tb≦Tc+Td1 is maintained for a prescribed time ts1 (for example, approximately 5 minutes) or more based on the measured chamber temperature Tb and the chamber setting temperature Tc (S12). Td1 is a constant (for example, approximately 0.1 degrees centigrade). Namely, as shown in FIG. 3, it is determined whether or not a state where the chamber temperature Tb within the chamber body 100 is within a prescribed range (for example, ±0.1 degrees centigrade) taking the chamber setting temperature Tc as a reference continues for a prescribed time ts1 or more.

When a state where the condition of Tc−Td1≦Tb≦Tc+Td1 is maintained for the prescribed time ts1 or more (Y), the microcomputer 401 determines that the chamber temperature Tb is stable and a chamber OK flag is erected (S13). On the other hand, when a state where the condition Tc−Td1≦Tb≦Tc+Td1 is satisfied is not maintained for the prescribed time ts1 or more (N), the microcomputer 401 lowers the chamber OK flag (S14).

After this, the microcomputer 401 calculates a predicted stable chamber temperature time from the external air temperature Tp, the chamber temperature Tb, and the chamber setting temperature Tc using a prescribed approximation etc. stored in the microscope apparatus (S15). The predicted stable chamber temperature time is a predicted period of time that elapses until when it is determined the chamber temperature Tb has become stable with a state of satisfying the condition of Tc−Td1≦Tb≦Tc+Td1 maintained for the prescribed time ts1 or more. Next, the microcomputer 401 outputs a control signal to the display unit 301 and displays the calculated predicted stable chamber temperature time at the display unit 301 (S16).

After this, a humidifier temperature Th is measured by the humidifier temperature sensor 212 and a signal for the measured humidifier temperature Th is inputted to the microcomputer 401 (S17 of FIG. 6).

The microcomputer 401 then determines whether or not a state where the condition of Th−Td2≦Tch≦Th+Td2 is satisfied is maintained for a prescribed time ts2 (for example, five minutes) or more based on the measured humidifier temperature Th and the humidifier setting temperature Tch (S18). Td2 is a constant (for example, approximately 0.2 degrees centigrade). Namely, it is determined whether or not a state where the temperature of the distilled water within the humidifier bottle 215, i.e. the humidifier temperature Th is within a prescribed range (for example, ±0.2 degrees centigrade) taking the humidifier setting temperature Tch as a reference continues for the prescribed time ts2 or more.

When a state where the condition of Th−Td2≦Tch≦Th+Td2 is satisfied is continued for the prescribed time ts2 or more (Y), the microcomputer 401 assumes that the humidifier temperature Th is stable and erects a humidifier OK flag (S19). On the other hand, when a state where the condition Th−Td2≦Tch≦Th+Td2 is satisfied is not maintained for the prescribed time ts2 or more (N), the microcomputer 401 lowers the humidifier OK flag (S20).

After this, the microcomputer 401 calculates a predicted stable humidifier temperature time from the external air temperature Tp, the humidifier temperature Th, and the humidifier setting temperature Tch using a prescribed approximation etc. in the possession of the microscope apparatus (S21). The predicted stable humidifier temperature time is specifically a predicted period of time that elapses until when it is determined that the humidifier temperature Th has become stable with a state of satisfying the condition of Th−Td2≦Tch≦Th+Td2 maintained for the prescribed time ts2 or more. Next, the microcomputer 401 outputs a control signal to the display unit 301 and displays the calculated predicted stable humidifier temperature time at the display unit 301 (S22).

After this, a microscope temperature Tmc of the microscope unit 150 is measured at the microscope temperature sensor 151 and a signal for the measured microscope temperature Tmc is inputted to the microcomputer 401 (S23).

The microcomputer 401 calculates a difference (Tm−Tn) between a maximum value Tm and a minimum value Tn for the microscope temperature Tmc within a prescribed time ts (for example, approximately 5 minutes) (S24). After this, it is determined whether or not a reference value Tf is greater than (Tm−Tn) (refer to FIG. 4) (S25). When shifting of focus of the image of the microscope unit 150 due to change in temperature is substantial, it is necessary to keep the reference value Tf small. For example, the reference value Tf is taken to be 0.2 to 0.3 degrees centigrade. When the reference value Tf is greater than (Tm−Tn) (Y), the microcomputer 401 determines that the microscope temperature Tmc is stable and erects a microscope OK flag (S26). On the other hand, when it is determined that a state satisfying the condition of a reference value Tf>(Tm−Tn) is not maintained for the prescribed time ts or more (N), the microcomputer 401 lowers the microscope OK flag (S27).

Next, the microcomputer 401 calculates a predicted stable microscope temperature time from the external air temperature Tp, the microscope temperature Tmc, and the difference (Tm−Tn) using an approximation etc. possessed by the microscope apparatus (S28). The predicted stable microscope temperature time is a predicted period of time that elapses until when it is determined that the microscope temperature Tmc has become stable. Next, the microcomputer 401 outputs a control signal to the display unit 301 and displays the calculated predicted stable humidifier temperature time at the display unit 301 (S29).

The microcomputer 401 then determines whether or not the chamber OK flag, the humidifier OK flag, and the microscope OK flag are all erected (S30). When the chamber OK flag, the humidifier OK flag, and the microscope OK flag are all erected (Y), the microcomputer 401 determines that the microscope apparatus is in a state where use is possible. The microcomputer 401 then outputs a control signal to the display unit 301 and displays that preparations for use of the microscope apparatus are complete, i.e. that a state is attained where observation using the microscope apparatus is possible, at the display unit 301 (S31). In this manner, it is displayed at the display unit 301 that the temperature of the whole of the microscope apparatus is stable and that superior observation is possible. This makes it possible to carry out observations with only a small drift in focal point.

Step S2 is returned to after it is displayed on the display unit 301 that preparations for use are complete, or when either of the chamber OK flag, the humidifier OK flag, or the microscope OK flag are not erected (N).

Figure 7:
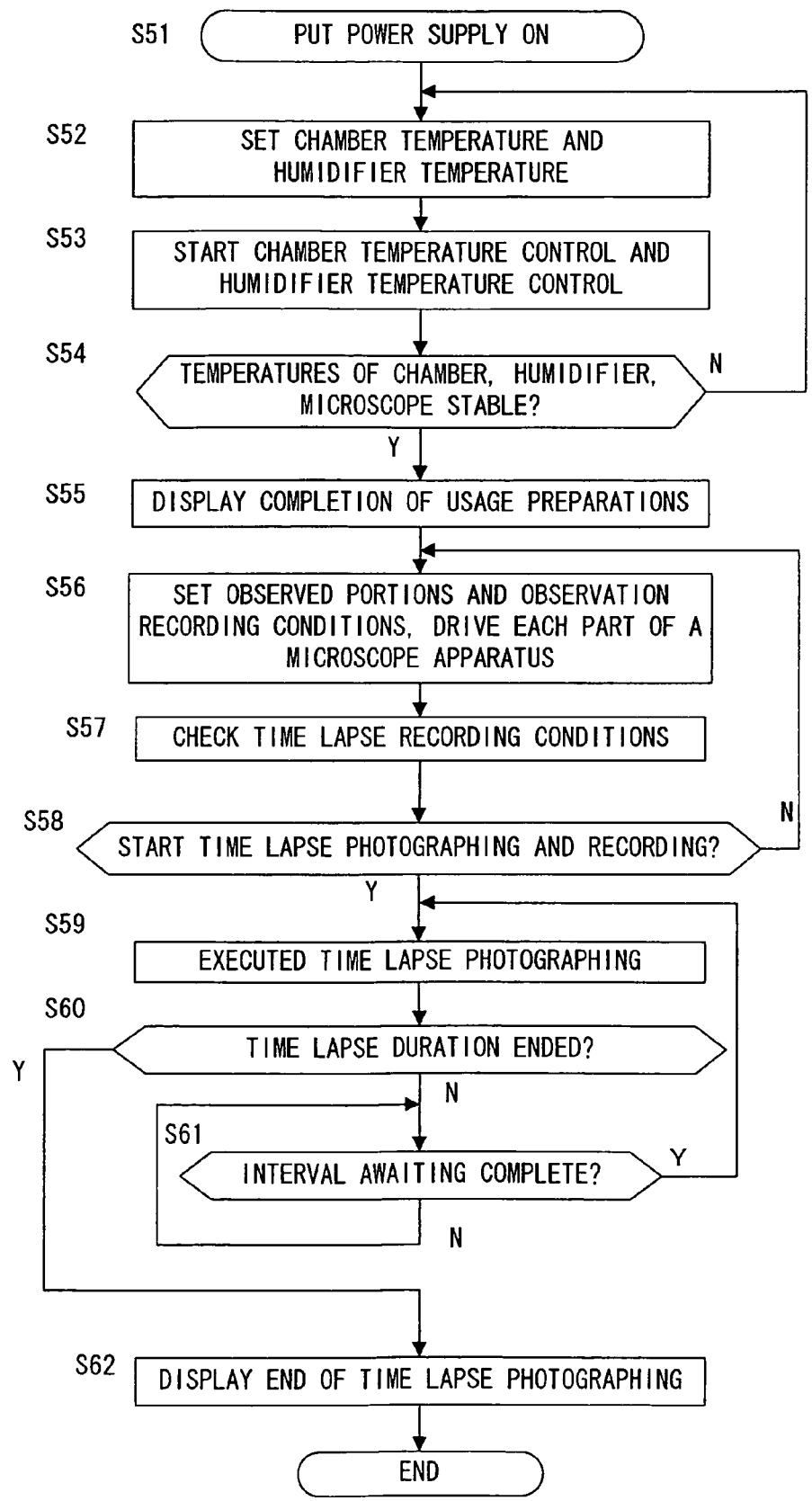
FIG. 7 is a flowchart explaining the time lapse photography used at the microscope apparatus.

FIG. 7 is a flowchart explaining a procedure for time lapse photographing employing the microscope apparatus. The control of the microcomputer 401 and the control of the personal computer 5 is shown collectively in the flowchart of FIG. 7 in order to explain the flow of the time lapse photography in a manner that is easy to understand.

First, a power supply of the microscope apparatus is turned on (S51).

Next, a chamber temperature (for example, 37 degrees centigrade) and a humidifier temperature (for example, 40 degrees centigrade) are set by operating an input device (for example, a keyboard) (not shown) of the personal computer 5 (S52). The chamber temperature and the humidifier temperature set by the personal computer 5 are sent to the chamber temperature setting circuit 250 and the humidifier temperature setting circuit 251 respectively via the communication interface, and set as the chamber setting temperature Tc and the humidifier setting temperature Tch.

The microcomputer 401 measures the chamber temperature Tb, the humidifier temperature Th, and the microscope temperature Tmc and starts control of each temperature (S53). Next, it is determined whether or not the temperatures of the chamber body 100, the humidifier 211, and the microscope unit 150 are stable (S54). When it is determined that the temperatures of the chamber body 100, the humidifier 211, and the microscope unit 150 are stable (Y), the microcomputer 401 outputs a control signal to the display unit 301 and displays that preparations for use of the microscope apparatus are complete at the display unit 301 (S55). On the other hand, when it is determined that the temperatures of the chamber body 100, the humidifier 211, and the microscope unit 150 are not yet stable, S52 is returned to and control of each temperature is repeated. This processing is carried out in accordance with the flowcharts of FIGS. 5 and 6.

After confirming the display of completion of the preparations for use on the display unit 301, the user opens the casing cover 82 and the chamber cover 21 and puts the Petri dish 20 housing the specimen into the chamber body 100. After placing the Petri dish 20 within the chamber body 100, the user closes the chamber cover 21 and the casing cover 82.

Next, the user implements selection of the portions of the specimen to be observed and the setting of observation recording conditions etc. using an operation interface consisting of the personal computer 5 and a GUI of the display 6. The microcomputer 401, that controls the microscope apparatus, controls a control apparatus (not shown) and drives each part of the microscope apparatus in accordance with operation of the personal computer 5 by the user (S56).

Specifically, the user carries out the following setting operations at the input device (for example, a keyboard and mouse) of the personal computer 5.

The user changes the settings for a relative position (XYZ direction) of the objective lens 26 with respect to the specimen, the amount of illuminating light, the method of observation (phase difference observation/fluorescence observation), and observation magnification.

The user searches for a plurality of locations intended for time lapse observation and recording within the specimen while looking at an image of the specimen displayed on the display 6 of the personal computer 5, and enters or records the recording conditions (recording interval, recording time (or number of recording cycles)) and the relative position.

The microcomputer 401, that controls the microscope, carries out the following settings in accordance with a signal from the personal computer 5 according to user operations inputted via the communication interface.

The LED light source 47 is turned on and light-modulated, the mercury lamp (not shown) is turned on and light-modulated, and the fluorescence filter cube 34 is switched over according to a switching instruction of the observation method.

The motor (not shown) is driven so that the image forming lens 38 is switched over to change optical magnification according to a magnification switching instruction.

The personal computer 5 then carries out the following check based on the inputted time lapse recording conditions (S57).

Is the estimated total recording size of the image to be recorded by the coldproof camera 300 within the capacity range of the personal computer 50 or externally connected image recording apparatus?

Is the set recording interval within the implementable range?

Next, it is determined whether or not time lapse photographing and recording has started (S58). The starting of time lapse photographing and recording is instructed according to the operation of the keyboard etc. of the personal computer 5.

When the time lapse photographing and recording has not started (N), S56 is returned to. When the time lapse photography and recording has started (Y), the personal computer 5 sends the recorded time lapse observation locations and the observation and recording conditions to the microcomputer 401 via the communication interface. The microcomputer 401 then executes the photographing and recording in the following manner (S59).

First, a first observation location within the specimen is photographed and recorded.

The objective lens 26 is moved to the designated XYZ coordinates.

The magnification is then switched over to the designated magnification.

The illuminating light source (transmission illuminating light source/fluorescent light source) is then switched over according to the set observation mode and the setting for the amount of illuminating light is changed.

After all of the photographing and recording conditions for the microscope unit 150 are adjusted, the coldproof camera 300 is driven and photographing is carried out.

In the case where the photographing and recording are to be performed on a single observation location in a plurality of conservation modes, after changing the settings for the observation mode and the amount of illuminating light, the coldproof camera 300 is driven and photographing is carried out.

The observation locations are then sequentially switched over between a second observation location, and a third observation location . . . until all the observation locations are photographed and recorded. How to change the setting is the same as for the case of the first observation location.

Next, the microcomputer 401 determines whether or not the time lapse interval (recording time) is complete (S60). When the time lapse interval is not complete (N), it is determined whether or not waiting for the interval is complete (S61). This determination is repeated until waiting for the interval is complete. When waiting for the interval is complete (Y), step S59 is returned to. When the time lapse interval is complete (Y), the microcomputer 401 outputs the control signal to the display unit 301 and completion of the time lapse photographing is displayed at the display unit 301.

In the time lapse photographing described above, the specimen (cells) is kept alive in a culture environment where the temperature, humidity, and $CO_2$ concentration are controlled. Photographing is therefore automatically carried out while always in focus and it is possible to record changes in the specimen over time.

The external air temperature Tp, the chamber temperature Tb, the humidifier temperature Th, and the microscope temperature Tmc are periodically checked even after the time lapse recording has started. The presence of an error is therefore displayed at the display unit 301 when the conditions no longer matches with the conditions for determining use of the microscope apparatus is possible and the conditions for determining completion of preparations.

According to this embodiment, it is possible to start time lapse photography after stabilizing the temperatures of the chamber body 100, the humidifier 211, and the microscope unit 150. It is therefore possible to prevent drifting of the focus from appearing due to changes in temperature of the microscope unit 150 occurring during photographing. It is therefore possible to start observation after checking not only the temperature conditions within the chamber body 100 and the temperature conditions of the humidifier 211 but also after checking the temperature of the microscope unit 150. It is therefore possible to suppress focus drift due to changes in temperature of the microscope unit 150 during observation.

It is also possible to check in advance and give notification as to whether or not the set temperature conditions, specifically the chamber setting temperature Tc set at the chamber temperature setting circuit 250 and the humidity setting temperature Tch set at the humidifier temperature setting circuit 251 conform with the temperature conditions for the chamber body 100 and the humidifier 211 measured by the temperature sensors 204 and 212. It is therefore possible to achieve compatibility with changes in room temperature etc. when there is no matching. Further, it is possible to know an estimated time for which an apparatus conforming to the various temperature conditions can be used. It is therefore possible to prepare for experiments without wastefulness.

It is also possible to configure the time lapse photographing to start automatically after completion of preparation of the microscope apparatus. Specifically, the user selects a portion of the specimen to be observed and sets the observation recording conditions etc. after the power supply for the microscope apparatus is turned on. The user instructs the start of the time lapse photographing and recording by operating a keyboard etc. of the personal computer 5. The microcomputer 401 of the microscope apparatus controls each part of the microscope apparatus according to set content and the personal computer 5 carries out the check in S57. After this, the microscope apparatus carries out chamber temperature control and humidifier temperature control. If the temperature of the chamber body 100, the humidifier 211, and the microscope unit 150 stabilizes, it is displayed at the display unit 301 that preparations for use of the microscope apparatus are complete. At the same time as this, the time lapse photographing and recording by the microscope apparatus is started automatically.

In the above embodiment, the display unit 301 is used as the notification device to make the observer aware visually that observation by microscope is possible. However, it is also possible, for example, to make the observer aware that observation by microscope is possible using sound.

It is also possible to determine whether or not observation by microscope is possible based on the output of the chamber temperature sensor 204 and the microscope temperature sensor 151. In this case, it is possible to omit the humidifier temperature sensor 212 that measures the temperature of the humidifier 211.

In the above, a description is given of various embodiments and modified examples but the present invention is by no means limited to the content of this description. Other aspects are also incorporated within the scope of the present invention and are considered as being within the range of the technological concept of the present invention.

What is claimed is:

1. A microscope apparatus comprising:
   a microscope unit;
   a chamber, arranged next to the microscope unit, that houses a specimen to be observed by the microscope unit;
   a humidifier, connected to the chamber, that humidifies the interior of the chamber;
   a chamber temperature sensor that measures a temperature within the chamber;
   a microscope temperature sensor that measures a temperature of the microscope unit; and
   a determination device that determines whether or not observation by microscope is possible based on outputs of the chamber temperature sensor and the microscope temperature sensor.

2. A microscope apparatus according to claim 1, further comprising:
a humidifier temperature sensor that measures a temperature of the humidifier, wherein:
the determination device determines whether or not observation by microscope is possible by further taking into consideration an output of the humidifier temperature sensor.

3. A microscope apparatus according to claim 2, further comprising:
a notification device that notifies as to whether or not observation by microscope is possible, wherein:
the determination device determines that observation by microscope is possible when the chamber temperature, the humidifier temperature, and the microscope temperature become substantially stable, and causes the notification device to notify that observation by microscope is possible.

4. A microscope apparatus according to claim 2, further comprising:
an external air temperature sensor that measures an external air temperature, wherein:
the determination device determines whether or not observation by microscope is possible by further taking into consideration an output by the external air temperature sensor.

5. A microscope apparatus according to claim 4, further comprising:
a chamber temperature setting circuit that sets the temperature of the chamber, wherein:
the external air temperature measured by the external air temperature sensor is taken to be Tp, a chamber setting temperature set by the chamber temperature setting circuit is taken to be Tc, and T1 and T2 are taken to be constants, and
the determination device causes the notification device to notify that the external air temperature is inappropriate when Tc−Tp is greater than T1, or when Tc−Tp is smaller than T2.

6. A microscope apparatus according to claim 2, further comprising:
a humidifier temperature setting circuit that sets the temperature of the humidifier, wherein:
the chamber temperature measured by the chamber temperature sensor is taken to be Tb, the humidifier temperature measured by the humidifier temperature sensor is taken to be Th, the humidifier setting temperature set by the humidifier temperature setting circuit is taken to be Tch, a maximum value for the microscope temperature measured by the microscope temperature sensor is taken to be Tm and a minimum value for the microscope temperature measured by the microscope temperature sensor is taken to be Tn, Tf is taken to be a reference value, and Td1 and Td2 are taken to be constants, and
the determination device determines that observation by microscope is possible when:
(1) |Tb−Tc|<Td1, and this condition is maintained for a prescribed time or more;
(2) |Th−Tch|<Td2, and this condition is maintained for a prescribed time or more; and
(3) (Tm−Tn)<Tf.

7. A microscope apparatus according to claim 3, wherein:
the determination device estimates a period of time that elapses until when observation by microscope becomes possible based on the external air temperature measured by the external air temperature sensor, the chamber temperature measured by the chamber temperature sensor, the microscope temperature measured by the microscope temperature sensor, and the humidifier temperature measured by the humidifier temperature sensor, and causes the notification device to notify of the estimated period of time.

* * * * *